(12) United States Patent
Liu et al.

(10) Patent No.: US 12,735,448 B2
(45) Date of Patent: Sep. 15, 2026

(54) CRYSTAL FORM OF 3-HYDROXY-5-PREGNANE-20-ONE DERIVATIVE, AND PREPARATION METHOD THEREFOR AND USE THEREOF

(71) Applicant: TWi Biotechnology, Inc., Taipei City (TW)

(72) Inventors: Fei Liu, Nanjing (CN); Gang Wu, Nanjing (CN); Xianchao Li, Nanjing (CN); Xiaobo Wang, Nanjing (CN); Jinwei Liu, Nanjing (CN)

(73) Assignee: TWi Biotechnology, Inc., Taipei City (TW)

( * ) Notice: Subject to any disclaimer, the term of this patent is extended or adjusted under 35 U.S.C. 154(b) by 459 days.

(21) Appl. No.: 18/276,321

(22) PCT Filed: Jan. 27, 2022

(86) PCT No.: PCT/CN2022/074412

§ 371 (c)(1),
(2) Date: Aug. 8, 2023

(87) PCT Pub. No.: WO2022/166774

PCT Pub. Date: Aug. 11, 2022

(65) Prior Publication Data

US 2024/0132536 A1 Apr. 25, 2024

(30) Foreign Application Priority Data

Feb. 8, 2021 (CN) ......................... 202110172486.7

(51) Int. Cl.
*C07J 41/00* (2006.01)

(52) U.S. Cl.
CPC .................................. *C07J 41/005* (2013.01)

(58) Field of Classification Search
CPC .... C07J 41/005; C07B 2200/13; A61K 31/57; A61P 25/00
See application file for complete search history.

(56) References Cited

U.S. PATENT DOCUMENTS 9,687,496 B2 6/2017 Backstrom et al.
2013/0245253 A1 9/2013 Marx et al.
(Continued)

FOREIGN PATENT DOCUMENTS

CN 103333216 A 10/2013
CN 102753181 B 9/2014
(Continued)

OTHER PUBLICATIONS

English translation International Search Report mailed Apr. 7, 2022 corresponding to PCT/CN2022/074412, 5 pages.

*Primary Examiner* — San Ming R Hui
(74) *Attorney, Agent, or Firm* — HSML P.C.

(57) ABSTRACT

The present invention provides a crystal of a compound represented by formula I as a 3-hydroxy-5-pregnane-20-one derivative and a preparation method therefor. Specifically, the present invention provides novel crystal forms A-C of the compound represented by formula I and a preparation method therefor. The novel crystal forms of the compound represented by formula I of the present invention have excellent thermal stability and mechanical stability, the preparation process thereof is simple, and the novel crystal forms have an excellent industrial implementation potential.

(Continued)

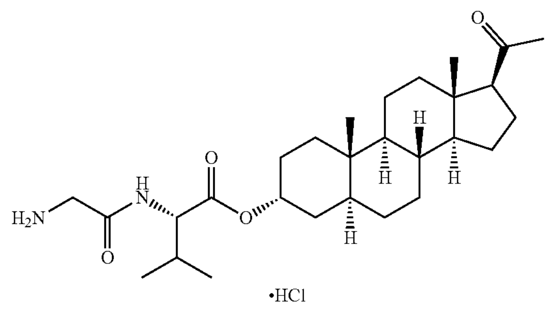

•HCl

9 Claims, 5 Drawing Sheets

(56) References Cited

U.S. PATENT DOCUMENTS

| | | | |
|---|---|---|---|
| 2017/0022245 | A1 | 1/2017 | Volkmann et al. |
| 2018/0221390 | A1 | 8/2018 | MacNevin et al. |
| 2019/0322698 | A1 | 10/2019 | Li et al. |
| 2022/0289788 | A1 | 9/2022 | Liu et al. |

FOREIGN PATENT DOCUMENTS

| | | | |
|---|---|---|---|
| CN | 108148106 | A | 6/2018 |
| CN | 108517001 | A | 9/2018 |
| WO | 2009-108804 | A2 | 9/2009 |
| WO | 2011-120044 | A1 | 9/2011 |
| WO | 2015-081170 | A2 | 6/2015 |
| WO | 2021-027744 | A1 | 2/2021 |

CRYSTAL FORM OF 3-HYDROXY-5-PREGNANE-20-ONE DERIVATIVE, AND PREPARATION METHOD THEREFOR AND USE THEREOF

TECHNICAL FIELD

The present invention relates to the field of pharmaceutical chemistry. In particular, the present invention relates to crystal forms of 3-hydroxyl-5-pregnane-20-one derivative and preparation methods as well as the use thereof for preventing or treating a disorder of the central nervous system.

BACKGROUND

Neuroactive steroids are active steroids in the nervous tissue, and the neuroactive steroids playing a key role in regulating the human body. Neuroactive steroids mainly comprise progesterone, pregnenolone, allopregnanolone, etc. Progesterone, pregnenolone and allopregnanolone are all produced by cholesterol through different metabolism pathways. Cholesterol transfers, under the mediation of a 18 kDa translin, from the outer membrane of the mitochondria to the inner membrane, produces pregnenolone through the metabolism of cytochrome P450 cholesterol side-chain cleavage enzyme, then produces progesterone through the metabolism of 3β-hydroxysteroid dehydrogenase, and continues to produce allopregnanolone through the metabolism of a series of enzyme reactions mediated by 5α-reductase and 3α-hydroxysteroid dehydrogenase. Neuroactive steroids can be used as anesthetics, tranquillizers, hypnotics, antianxietics, antidepressants and anticonvulsants.

Allopregnanolone has been a hotspot of studies in recent years, and it has been pointed out as early as in 1986 that allopregnanolone is a positive modulator of the $GABA_A$ receptor. However, it was not until the year 2006 when people finally found that allopregnanolone may essentially bind to the α and β subunits of the $GABA_A$ receptor, increase the open frequency of chloride ion channel in the receptor, and decrease the nerve excitability so as to produce stabilizing and anxiolytic effects. It has been reported in the literature that during different periods of the menstrual cycle, the levels of progesterone and the metabolites thereof in vivo are different. Before the beginning of the menstrual cycle, the levels of progesterone and the metabolite thereof decrease, which can induce premenstrual syndrome (PMS), that is to say, before the beginning of the menstrual cycle, some symptoms would repeatedly appear but they would disappear after the menstrual cycle, such as stress, anxiety and migraine. Postpartum depression would also be related to abnormal levels of progesterone and the metabolite thereof, and the concentration of allopregnanolone in the plasma of a healthy pregnant woman increases with the development of pregnancy, and after delivery, the concentration of allopregnanolone would drastically decrease. Researches have suggested that the decrease of the content of allopregnanolone is considered to be closely related to the occurrence and development of many mental disorders such as anxiety, depression and tremor, and the exogenous administration of allopregnanolone can significantly improve the above-mentioned psychiatric symptoms.

However, allopregnanolone exhibits a low water solubility and a poor oral availability, with a human plasma half-life period being about 45 minutes, and can be rapidly metabolized. The marketed Zulresso is a water-soluble, sulfobutyl β-cyclodextrin-based preparation of allopregnanolone that is injected intravenously to produce a stable physiological concentration of allopregnenolone. However, an intravenous infusion of up to 60 hours are required for Brexanolone, which causes poor compliance of a patient.

In addition, it is also known to a skilled person that different crystalline forms of a drug will result in significant differences in bioavailability, solubility, dissolution rate, chemical and physical stability, melting point, colour, filtrability, density, flowability and the like. The study of the polymorph of a drug is beneficial in finding forms of the drug with better physicochemical properties or better processing forms, thereby broadening formulation forms of the drug and developing valuable formulation forms for the convenience of various kinds of people.

Therefore, there is a need in the art not only for a derivative of allopregnanolone with improved solubility, reduced administration time, and stable physiological concentrations in the body for a long period of time; there is also a need for the development of different crystalline forms of such derivative with excellent properties.

SUMMARY OF THE INVENTION

The purpose of the present invention is to provide a derivative of 3-hydroxy-5-pregnan-20-one and a polymorph thereof, wherein said derivative can be used in the preparation of a drug for preventing or treating a disorder of the central nervous system and such derivative has improved solubility, is stable in storage, is easy to be administered, and has a good compliance of a patient when administered.

The purpose of the present invention is to provide a polymorph of the 3-hydroxy-5-pregnan-20-one derivative as said above, wherein said polymorph can have excellent thermodynamic and mechanical stability.

In the first aspect, the present invention provides a crystalline form A of a compound of formula I and the X-ray powder diffraction pattern thereof shows characteristic peaks at following 2θ angles: 12.66±0.2°, 13.53±0.2°, 16.75±0.2° and 25.39±0.2°

I

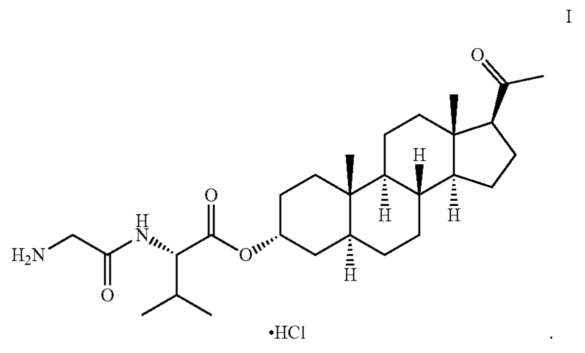

•HCl

In some embodiments of the present invention, the X-ray powder diffraction pattern of the above crystalline form A shows characteristic peaks at following 2θ angles: 11.96±0.2°, 12.66±0.2°, 13.53±0.2°, 14.51±0.2°, 16.75±0.2° and 25.39±0.2°.

In some embodiments of the present invention, the X-ray powder diffraction pattern of the above crystalline form A shows characteristic peaks at following 2θ angles: 11.96±0.2°, 12.66±0.2°, 13.53±0.2°, 14.51±0.2°, 16.75±0.2°, 19.27±0.2°, 22.19±0.2° and 25.39±0.2°.

In some embodiments of the present invention, the X-ray powder diffraction pattern of the above crystalline form A shows characteristic peaks at following 2θ angles: 11.96±0.2°, 12.66±0.2°, 13.53±0.2°, 14.51±0.2°, 16.75±0.2°, 19.27±0.2°, 22.19±0.2°, 25.39±0.2°, 26.23±0.2°, 31.87±0.2° and 35.34±0.2°.

In some embodiments of the present invention, the X-ray powder diffraction pattern of the above crystalline form A shows characteristic peaks at following 2θ angles: 11.96±0.2°, 12.66±0.2°, 13.53±0.2°, 13.88±0.2°, 14.51±0.2°, 15.81±0.2°, 16.75±0.2°, 17.99±0.2°, 18.99±0.2°, 19.27±0.2°, 21.95±0.2°, 22.19±0.2°, 25.39±0.2°, 26.23±0.2°, 31.87±0.2° and 35.34±0.2°.

In some embodiments of the present invention, the peak positions and intensities of the characteristic peaks in the X-ray powder diffraction pattern of the above crystalline form A are shown in Table 1:

TABLE 1 peak positions and intensities of the characteristic peaks in the X-ray powder diffraction pattern of crystalline form A

| Number | 2θ angle (°) | relative intensity (%) |
|---|---|---|
| 1 | 11.96 | 21.12 |
| 2 | 12.66 | 23.74 |
| 3 | 13.53 | 49.52 |
| 4 | 13.88 | 8.31 |
| 5 | 14.51 | 19.45 |
| 6 | 15.81 | 11.30 |
| 7 | 16.75 | 53.89 |
| 8 | 17.99 | 13.11 |
| 9 | 18.99 | 13.44 |
| 10 | 19.27 | 16.18 |
| 11 | 21.95 | 12.16 |
| 12 | 22.19 | 58.99 |
| 13 | 25.39 | 100.00 |
| 14 | 26.23 | 18.60 |
| 15 | 31.87 | 58.49 |
| 16 | 35.34 | 20.81 |

In some embodiments of the present invention, the XRPD pattern of the above crystalline form A is shown in FIG. 1, that is, it has characteristics represented by the XRPD pattern as shown in FIG. 1.

In some embodiments of the present invention, the resolution data of XRPD pattern for the above crystalline form A is shown in Table 2:

TABLE 2 resolution data of XRPD pattern for crystalline form A

| Number | 2θ angle (°) | interplanar spacing (Å) | relative intensity (%) |
|---|---|---|---|
| 1 | 11.96 | 7.40 | 21.12 |
| 2 | 12.66 | 7.00 | 23.74 |
| 3 | 13.53 | 6.54 | 49.52 |
| 4 | 13.88 | 6.38 | 8.31 |
| 5 | 14.51 | 6.11 | 19.45 |
| 6 | 15.81 | 5.60 | 11.30 |
| 7 | 16.75 | 5.29 | 53.89 |
| 8 | 17.99 | 4.93 | 13.11 |
| 9 | 18.99 | 4.67 | 13.44 |
| 10 | 19.27 | 4.61 | 16.18 |
| 11 | 21.95 | 4.05 | 12.16 |
| 12 | 22.19 | 4.01 | 58.99 |
| 13 | 25.39 | 3.51 | 100.00 |
| 14 | 26.23 | 3.40 | 18.60 |

TABLE 2-continued resolution data of XRPD pattern for crystalline form A

| Number | 2θ angle (°) | interplanar spacing (Å) | relative intensity (%) |
|---|---|---|---|
| 15 | 31.87 | 2.81 | 58.49 |
| 16 | 35.34 | 2.54 | 20.81 |

In some embodiments of the present invention, the differential scanning calorimetry curve of the above crystalline form A has an endothermic peak at 216.85° C.±3° C.

In some embodiments of the present invention, the DSC pattern of the above crystalline form A is shown in FIG. 2, that is, it has characteristics represented by the DSC pattern as shown in FIG. 2.

In some embodiments of the present invention, the method for preparing crystalline form A of the above compound of formula I comprises following steps:

(1) mixing the compound of formula I with a solvent;

(2) filtering and drying the mixture of step (1);

wherein said solvent is selected from one or more of methanol, ethanol, isopropanol, acetone, butanone, ethyl acetate, isopropyl acetate, methyl tert-butyl ether, n-heptane, toluene; and preferably ethanol, isopropanol, ethyl acetate.

In some embodiments of the present invention, step (1) is carried out under a heated condition.

In some embodiments of the present invention, in step (1), the temperature for heating is about 60 to 70° C., preferably about 65° C.

In some embodiments of the present invention, in step (1), the compound of formula I is added and then stirred for, for example, 6 to 18 hours, preferably 12 hours.

In some embodiments of the present invention, in step (2), the mixture is cooled to, for example, 0 to 30° C., preferably to 20° C., and then filtered.

In some embodiments of the present invention, in step (2), the mixture can be stirred after being cooled as required for, for example, 6 to 24 hours, preferably 18 hours.

In some embodiments of the present invention, in step (2), the mixture is optionally washed with a solvent and then dried, and said solvent for washing is selected from a group consisting of methanol, ethanol, acetone, ethyl acetate, methanol ether, n-heptane, and toluene, and preferably ethyl acetate.

In the second aspect, the present invention provides a crystalline form B of a compound of formula I and the X-ray powder diffraction pattern thereof shows characteristic peaks at following 2θ angles: 10.69±0.2°, 13.17±0.2°, 13.37±0.2° and 15.22±0.2°

I

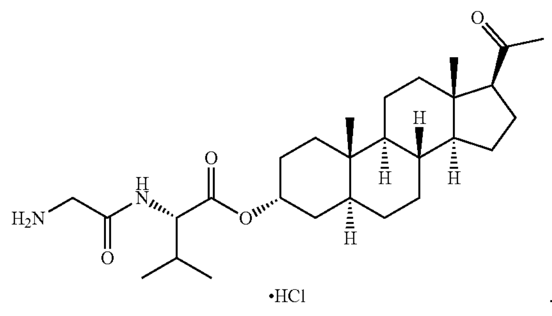

•HCl .

In some embodiments of the present invention, the X-ray powder diffraction pattern of the above crystalline form B shows characteristic peaks at following 2θ angles: 4.26±0.2°, 4.50±0.2°, 10.69±0.2°, 13.17±0.2°, 13.37±0.2°, and 15.22±0.2°.

In some embodiments of the present invention, the X-ray powder diffraction pattern of the above crystalline form B shows characteristic peaks at following 2θ angles: 4.26±0.2°, 4.50±0.2°, 10.69±0.2°, 12.88±0.2°, 13.17±0.2°, 13.37±0.2°, 15.22±0.2° and 15.81±0.2°.

In some embodiments of the present invention, the X-ray powder diffraction pattern of the above crystalline form B shows characteristic peaks at following 2θ angles: 4.26±0.2°, 4.50±0.2°, 8.77±0.2°, 10.69±0.2°, 12.14±0.2°, 12.88±0.2°, 13.17±0.2°, 13.37±0.2°, 15.22±0.2°, 15.81±0.2°, 25.35±0.2° and 29.04±0.2°.

In some embodiments of the present invention, the X-ray powder diffraction pattern of the above crystalline form B shows characteristic peaks at following 2θ angles: 4.26±0.2°, 4.50±0.2°, 8.77±0.2°, 10.69±0.2°, 12.14±0.2°, 12.88±0.2°, 13.17±0.2°, 13.37±0.2°, 15.22±0.2°, 15.81±0.2°, 17.37±0.2°, 21.47±0.2°, 23.19±0.2°, 25.35±0.2°, 26.83±0.2°, 29.04±0.2°, 30.52±0.2° and 30.79±0.2°.

In some embodiments of the present invention, the peak positions and intensities of the characteristic peaks in the X-ray powder diffraction pattern of the above crystalline form B are shown in Table 3:

TABLE 3 peak positions and intensities of the characteristic peaks in the X-ray powder diffraction pattern of crystalline form B

| Number | 2θ angle (°) | relative intensity (%) |
|---|---|---|
| 1 | 4.260 | 17.6 |
| 2 | 4.497 | 14.7 |
| 3 | 8.773 | 7.6 |
| 4 | 10.686 | 11.5 |
| 5 | 12.143 | 6.7 |
| 6 | 12.876 | 27.9 |
| 7 | 13.171 | 62.5 |
| 8 | 13.366 | 100 |
| 9 | 15.223 | 47.6 |
| 10 | 15.813 | 27.2 |
| 11 | 17.371 | 10.1 |
| 12 | 21.469 | 20.5 |
| 13 | 23.186 | 12.1 |
| 14 | 25.351 | 21.4 |
| 15 | 26.831 | 15.4 |
| 16 | 29.038 | 15.0 |
| 17 | 30.518 | 11.2 |
| 18 | 30.792 | 13.1 |

In some embodiments of the present invention, the XRPD pattern of the above crystalline form B is shown in FIG. 3, that is, it has characteristics represented by the XRPD pattern as shown in FIG. 3.

In some embodiments of the present invention, the resolution data of XRPD pattern for the above crystalline form B is shown in Table 4:

TABLE 4 resolution data of XRPD pattern for crystalline form B

| Number | 2θ angle (°) | interplanar spacing (Å) | relative intensity (%) |
|---|---|---|---|
| 1 | 4.260 | 20.7270 | 17.6 |
| 2 | 4.497 | 19.6332 | 14.7 |
| 3 | 8.773 | 10.0716 | 7.6 |
| 4 | 10.686 | 8.2718 | 11.5 |
| 5 | 12.143 | 7.2823 | 6.7 |
| 6 | 12.876 | 6.8696 | 27.9 |
| 7 | 13.171 | 6.7162 | 62.5 |
| 8 | 13.366 | 6.6186 | 100 |
| 9 | 15.223 | 5.8154 | 47.6 |
| 10 | 15.813 | 5.5998 | 27.2 |
| 11 | 17.371 | 5.1008 | 10.1 |
| 12 | 21.469 | 4.1355 | 20.5 |
| 13 | 23.186 | 3.8330 | 12.1 |
| 14 | 25.351 | 3.5103 | 21.4 |
| 15 | 26.831 | 3.3200 | 15.4 |
| 16 | 29.038 | 3.0725 | 15.0 |
| 17 | 30.518 | 2.9268 | 11.2 |
| 18 | 30.792 | 2.9014 | 13.1 |

In some embodiments of the present invention, the differential scanning calorimetry curve of the above crystalline form B has endothermic peaks near 120.67° C. and 226.10° C.

In some embodiments of the present invention, the differential scanning calorimetry curve of the above crystalline form B has endothermic peaks at 120.67° C.±3° C. and 226.10° C.±3° C.

In some embodiments of the present invention, the DSC pattern of the above crystalline form B is shown in FIG. 4, that is, it has characteristics represented by the DSC pattern as shown in FIG. 4.

In some embodiments of the present invention, the TGA pattern of the above crystalline form B is shown in FIG. 5, that is, it has characteristics represented by the TGA pattern as shown in FIG. 5.

In some embodiments of the present invention, the thermogravimetric analysis curve of the above crystalline form B has a weight-loss peak with a weight loss of up to 6.475±0.5%; and in particular, the thermogravimetric analysis curve of crystalline form B has a weight loss peak at 50° C.-125° C.

In some embodiments of the present invention, the method for preparing crystalline form B of the above compound of formula I comprises following steps:

(1) mixing the compound of formula I with a solvent;

(2) filtering and drying the mixture of step (1);

wherein said solvent is selected from water, methanol mixed with water, ethanol mixed with water, acetone mixed with water or acetonitrile mixed with water, preferably water or ethanol mixed with water.

In some embodiments of the present invention, step (1) is carried out under a heated condition.

In some embodiments of the present invention, in step (1), the temperature for heating is about 65 to 75° C., preferably about 70° C.

In some embodiments of the present invention, in step (1), the compound of formula I is added and then stirred.

In some embodiments of the present invention, in step (2), the mixture is cooled to, for example, 0 to 30° C., preferably to 2 to 8° C., and then filtered.

In some embodiments of the present invention, in step (2), the mixture can be stirred after being cooled as required for, for example, 15 to 22 hours, preferably 18 hours.

In some embodiments of the present invention, in step (2), the mixture is optionally washed with a solvent and then dried, and said solvent for washing is selected from water, methanol mixed with water, ethanol mixed with water, acetone mixed with water or acetonitrile mixed with water, preferably water or ethanol mixed with water.

In the third aspect, the present invention provides a crystalline form C of a compound of formula I and the X-ray powder diffraction pattern thereof shows characteristic peaks at following 2θ angles: 6.77±0.2°, 7.08±0.2°, 8.34±0.2° and 12.46±0.2°

I

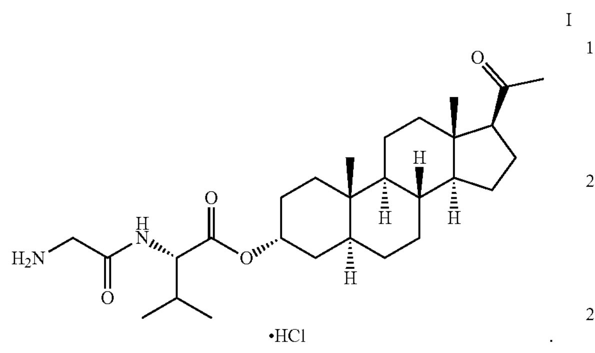

•HCl

.

In some embodiments of the present invention, the X-ray powder diffraction pattern of the above crystalline form C shows characteristic peaks at following 2θ angles: 6.77±0.2°, 7.08±0.2°, 8.34±0.2°, 12.46±0.2°, 17.60±0.2° and 17.92±0.2°.

In some embodiments of the present invention, the X-ray powder diffraction pattern of the above crystalline form C shows characteristic peaks at following 2θ angles: 6.77±0.2°, 7.08±0.2°, 8.34±0.2°, 12.46±0.2°, 13.21±0.2°, 16.52±0.2°, 17.60±0.2° and 17.92±0.2°.

In some embodiments of the present invention, the X-ray powder diffraction pattern of the above crystalline form C shows characteristic peaks at following 2θ angles: 6.77±0.2°, 7.08±0.2°, 8.34±0.2°, 11.02±0.2, 12.46±0.2°, 13.21±0.2°, 14.20±0.2, 15.06±0.2, 16.52±0.2°, 17.60±0.2°, 17.92±0.2 and 20.86±0.2.

In some embodiments of the present invention, the X-ray powder diffraction pattern of the above crystalline form C shows characteristic peaks at following 2θ angles: 6.77±0.2°, 7.08±0.2°, 8.34±0.2°, 10.61±0.2, 11.02±0.2, 12.46±0.2°, 13.21±0.2°, 13.76±0.2, 14.20±0.2, 14.63±0.2, 15.06±0.2, 15.75±0.2, 16.52±0.2°, 17.60±0.2°, 17.92±0.2, 19.14±0.2, 20.86±0.2, 24.76±0.2 and 26.46±0.2.

In some embodiments of the present invention, the peak positions and intensities of the characteristic peaks in the X-ray powder diffraction pattern of the above crystalline form C are shown in Table 5:

TABLE 5 peak positions and intensities of the characteristic peaks in the X-ray powder diffraction pattern of crystalline form C

| Number | 2θ angle (°) | relative intensity (%) |
|---|---|---|
| 1 | 6.766 | 100.00 |
| 2 | 7.079 | 43.9 |
| 3 | 8.342 | 25.0 |
| 4 | 10.608 | 10.7 |
| 5 | 11.024 | 19.5 |
| 6 | 12.462 | 71.8 |
| 7 | 13.212 | 23.2 |
| 8 | 13.764 | 11.4 |
| 9 | 14.197 | 19.8 |
| 10 | 14.629 | 15.9 |
| 11 | 15.063 | 38.8 |
| 12 | 15.753 | 16.4 |
| 13 | 16.521 | 27.3 |
| 14 | 17.605 | 47.5 |
| 15 | 17.921 | 34.1 |
| 16 | 19.143 | 17.0 |
| 17 | 20.858 | 27.5 |
| 18 | 24.762 | 20.7 |
| 19 | 26.457 | 13.6 |

In some embodiments of the present invention, the XRPD pattern of the above crystalline form C is shown in FIG. 6, that is, it has characteristics represented by the XRPD pattern as shown in FIG. 6.

In some embodiments of the present invention, the resolution data of XRPD pattern for the above crystalline form c is shown in Table 6:

TABLE 6 resolution data of XRPD pattern for crystalline form C

| Number | 2θ angle (°) | interplanar spacing (Å) | relative intensity (%) |
|---|---|---|---|
| 1 | 6.766 | 13.0535 | 100.00 |
| 2 | 7.079 | 12.4772 | 43.9 |
| 3 | 8.342 | 10.5905 | 25.0 |
| 4 | 10.608 | 8.3326 | 10.7 |
| 5 | 11.024 | 8.0195 | 19.5 |
| 6 | 12.462 | 7.0970 | 71.8 |
| 7 | 13.212 | 6.6958 | 23.2 |
| 8 | 13.764 | 6.4284 | 11.4 |
| 9 | 14.197 | 6.2333 | 19.8 |
| 10 | 14.629 | 6.0503 | 15.9 |
| 11 | 15.063 | 5.8767 | 38.8 |
| 12 | 15.753 | 5.6210 | 16.4 |
| 13 | 16.521 | 5.3613 | 27.3 |
| 14 | 17.605 | 5.0336 | 47.5 |
| 15 | 17.921 | 4.9455 | 34.1 |
| 16 | 19.143 | 4.6324 | 17.0 |
| 17 | 20.858 | 4.2552 | 27.5 |
| 18 | 24.762 | 3.5925 | 20.7 |
| 19 | 26.457 | 3.3661 | 13.6 |

In some embodiments of the present invention, the differential scanning calorimetry curve of the above crystalline form C has an endothermic peak at 179.31° C.±3° C.

In some embodiments of the present invention, the DSC pattern of the above crystalline form C is shown in FIG. 7, that is, it has characteristics represented by the DSC pattern as shown in FIG. 7.

In some embodiments of the present invention, the method for preparing the above crystalline form C of the compound of formula I comprises following steps:

(1) mixing the compound of formula I with solvent 1;

(2) adding solvent 2;

(3) filtering and drying the mixture of step (2);

wherein said solvent 1 is selected from one or more of methanol, ethanol, isopropanol, n-propanol, and tetrahydrofuran; and solvent 2 is selected from a group consisting of acetone, ethyl acetate, methyl tert-butyl ether, n-heptane, and toluene.

In some embodiments of the present invention, step (1) is carried out under a heated condition.

In some embodiments of the present invention, in step (1), the temperature for heating is about 60 to 70° C., preferably about 65° C.

In some embodiments of the present invention, in step (1), the compound of formula I is added and then stirred for, for example, 6 to 18 hours, preferably 12 hours.

In some embodiments of the present invention, the addition process of step (2) is carried out at a temperature of about 60 to 70° C., preferably about 65° C.

In some embodiments of the present invention, in step (3), the mixture is cooled to, for example, 0 to 30° C., preferably to 20° C., and then filtered.

In some embodiments of the present invention, in step (3), the mixture can be stirred after being cooled as required for, for example, 15 to 22 hours, preferably 18 hours.

In some embodiments of the present invention, in step (3), the mixture is optionally washed with a solvent and then dried, and said solvent for washing is selected from methanol, ethanol, acetone, ethyl acetate, methyl tert-butyl ether, n-heptane, toluene, preferably ethanol and methyl tert-butyl ether.

In the fourth aspect, the present invention provides a pharmaceutical composition, and said pharmaceutical composition comprises the above crystalline form A, crystalline form B or crystalline form C and optionally a pharmaceutically acceptable excipient.

In some embodiments of the present invention, said pharmaceutical composition comprises the above crystalline form A and optionally a pharmaceutically acceptable excipient.

In some embodiments of the present invention, said pharmaceutical composition is used for treating or preventing a disorder of the central nervous system in a mammal (e.g., a human).

In the fifth aspect, the present invention provides the use of the above crystalline form A, crystalline form B, or crystalline form C in the preparation of a drug for treating or preventing a disorder of the central nervous system in a mammal (e.g., a human).

In some embodiments of the present invention, the present invention provides the use of the above crystalline form A in the preparation of a drug for treating or preventing a disorder of the central nervous system in a mammal (e.g., a human).

In the sixth aspect, the present invention provides a method for treating or preventing a disorder of the central nervous system in a mammal (e.g., a human), and said method comprises administering to the mammal (e.g., a human) a therapeutically effective amount of a compound of formula (I), crystalline form A of the compound of formula I, a pharmaceutical composition comprising the crystalline form A of the compound of formula I, crystalline form B of the compound of formula I, a pharmaceutical composition comprising the crystalline form B of the compound of formula I, crystalline form C of the compound of formula I, and a pharmaceutical composition comprising the crystalline form C of the compound of I.

In some embodiments of the present invention, said method comprises administering to a mammal (e.g., a human) a therapeutically effective amount of a compound of formula (I), crystalline form A of the compound of formula I, a pharmaceutical composition comprising the crystalline form A of the compound of formula I.

In some embodiments of the present invention, said disorder of the central nervous system includes, but is not limited to, tremor, sleep disorders, depression, psychotic depressive illness, bipolar disorder, anxiety disorders, stress reactions, post-traumatic stress disorder, compulsive disorders, schizophrenia, affective schizophrenia, epilepsy, seizures, memory disorders and/or cognitive disorders, dementia, movement disorders, personality disorders, autism, autistic disorder of a single etiology, pain, traumatic brain injury, vascular disorders, substance abuse disorders, and/or withdrawal syndromes or tinnitus; or said disorder of the central nervous system includes, but is not limited to, idiopathic tremor, epilepsy, clinical depression, postnatal or postpartum depression, atypical depression, psychotic major depression, catatonic depression, seasonal affective disorder, dysphoria, double depression, depressive personality disorder, recurrent transient depression, mild depressive disorder, bi-directional psychotic or manic-depressive disorder, post-traumatic stress disorder, depression due to chronic medical conditions, treatment-resistant depression, refractory depression, suicidal tendency, suicidal ideation, suicidal behaviour, traumatic brain injury, generalised anxiety disorder, social anxiety disorder, attention deficit hyperactivity disorder, dementia, Huntington's chorea, Parkinson's disease, neuropathic pain, injury-related pain syndromes, acute pain, chronic pain, stroke, ischemia, vascular malformations, addiction to opioids, cocaine and/or alcohol addiction or insomnia.

It should be understood that, within the scope of the present invention, each of the above-mentioned technical features of the present invention and each of the technical features specifically described hereinafter (e.g., embodiments) may be combined with each other to constitute a new or preferred technical solution, which for conciseness, will not be repeated herein one by one.

MODES FOR CARRYING OUT THE INVENTION

Figure 1:
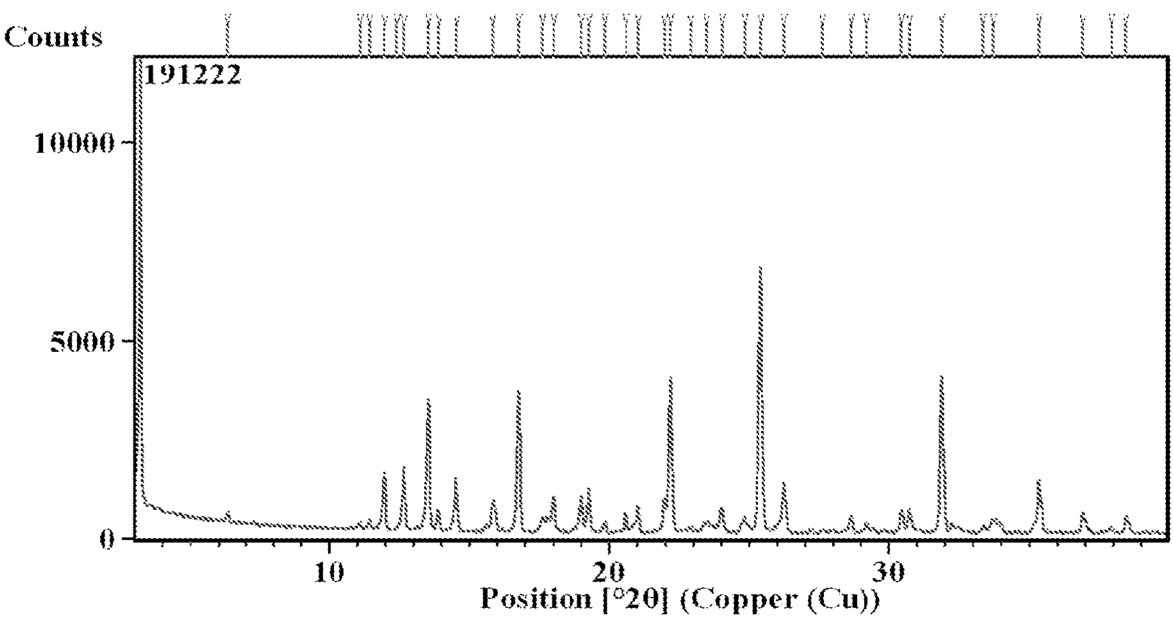
FIG. 1 shows XRPD pattern of crystalline form A of the 3-hydroxy-5-pregnan-20-one derivative of the present invention.

After extensive and intensive study, the present inventors have unexpectedly found a derivative of allopregnanolone, which can significantly improve the water solubility of allopregnanolone, have a certain storage stability in an aqueous solution, and be formulated into a long-acting, and sustained-release preparation with little individual difference after being administered. The preparation formulated from the derivative can maintain an effective physiological concentration of allopregnanolone in vivo for a relatively long time and is convenient to be administered, thus having the advantages of improving the patient's compliance.

Based on the derivative, the present inventors have discovered crystalline form A, crystalline form B, crystalline form C of the derivative, and said crystalline forms have advantages in at least one of physical stability, thermodynamic stability and mechanical stability, etc. The present invention has been completed on this basis.

Terms

As used herein, "the derivative of the present invention", "the derivatives of 3-hydroxy-5-pregnan-20-one", "the derivatives of allopregnanolones" have the same meaning and can be used interchangeably. All of these terms refer to the compounds shown of formula I below:

I

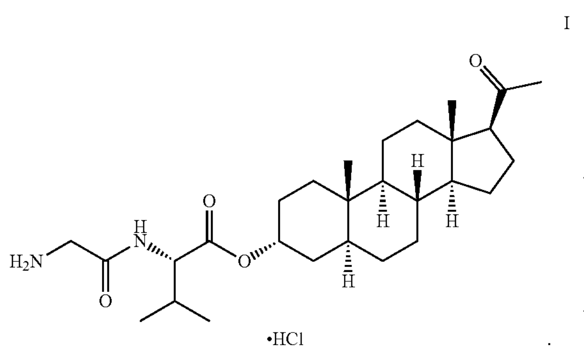

Herein, the chemical name of the compound of formula I is: glycine-L-valine 3α-hydroxy-5α-pregnan-20-one ester hydrochloride.

Polymorphism

It is known to a skilled person that a solid exists in an amorphous form or crystalline form. In the case of the crystalline form, molecules are localised within the sites of a three-dimensional lattice. When a compound is crystallised from a solution or slurry, it can crystallise in different spatial arrangements (a property known as the "polymorphism phenomenon"), thereby forming crystals with different crystalline forms, which are known as "polymorphs". Different polymorphs of a given substance may differ from each other in one or more physical properties (e.g., solubility and rate of dissolution, true specific gravity, crystalline shape, mode of accumulation, mobility and/or solid state stability).

The polymorphs of a compound may exhibit different melting points, hygroscopicity, stability, solubility, bioavailability, bioactivity, and mobility, and the like, which are important factors affecting drugability.

As used herein, the terms "crystal", "crystal of the present invention", "polymorph", "polymorph of the present invention", and the like, can be used interchangeably. For example, the crystalline form of the crystal described in the first aspect of the present invention is crystalline form A or named as crystal A.

Further, as used herein, all of the terms "polymorph of a derivative of the present invention", "polymorph of a derivative of 3-hydroxy-5-pregnan-20-one", and "polymorph of a derivative of allopregnanolone" refer to the crystalline form of the compound shown in Formula I.

Crystallization

Crystallisation on a production scale can be achieved by manipulating a solution such that the solubility limit of a compound of interest is exceeded. This can be accomplished by a variety of methods, for example, by dissolving the compound at a relatively high temperature and then cooling the solution below the saturation limit. Alternatively the liquid volume may be reduced by boiling, evaporation at atmospheric pressure, vacuum-drying or by some other methods. Or, the solubility of a compound of interest may be reduced by adding an anti-solvent or a solvent in which the compound has a low solubility or a mixture of such solvents. Another optional method is to adjust the pH to reduce the solubility. A detailed description of crystallisation can be found in Crystallization, 3rd edition, J W Mullens, Butterworth-Heineman Ltd. 1993, ISBN 0750611294.

The optimisation of crystallisation may comprise inoculating crystals of the desired form as crystal seeds into the crystallisation medium. Alternatively, a combination of the above strategies can be used in many crystallisation methods. For example, the compound of interest may be dissolved in a solvent at elevated temperatures, followed by the addition of an appropriate volume of anti-solvent in a controlled manner to bring the system just below the saturation level. At this point, crystal seeds of the desired form can be added (and the integrity of the crystal seeds is maintained) and the system are cooled to complete crystallisation.

In the present invention, crystals of the compound of formula I may be obtained by dissolving the compound of formula I in a solvent; subsequently cooling the resulting solution, or slowly evaporating the resulting solution, or adding an anti-solvent to the resulting solution to allow crystals of the compound of formula I to precipitate. After the crystals of the compound of formula I are obtained, the obtained crystals of the compound of formula I may also be optionally dried.

In a specific embodiment, said solvent is one or more selected from of the following group: water, methanol, ethanol, acetone, ethyl acetate, methanol ether, n-heptane, toluene.

In a preferred embodiment, in step (1), the temperature may be appropriately raised to promote the dissolution of the compound of formula I.

In a preferred embodiment, said cooling is to cool the solution of the compound of formula I to 20-30° C.

Solvate

During the contact between a compound or drug molecule and a solvent molecule, it is difficult to avoid the formation of a co-crystal between a solvent molecule and a compound molecule, caused by both external and internal conditions, which remains the solvent molecule in the solid substance. The substance formed after the crystallisation of the compound with the solvent is called a solvate. The types of solvents that tend to form solvates with organic compounds are water, methanol, benzene, ethanol, ether, aromatics, and heterocyclic aromatic hydrocarbons.

Hydrates are special solvates. In the pharmaceutical industry, hydrates possess values for separate discussion due to their special characteristics in the synthesis of APIs, in drug formulation, in drug storage and in the evaluation of drug activity.

In the present invention, the crystal of the compound shown in formula I can be a non-solvate or a solvate. For example, crystalline form B of the present invention is a hydrate.

Pharmaceutical Compositions of the Present Invention and the Administration Thereof Based on the polymorphs of 3-hydroxy-5-pregnan-20-one derivative of the present invention, the present invention further provides a pharmaceutical composition comprising said polymorphs. Said pharmaceutical composition has therapeutic effects of treating diseases caused by abnormalities of the central nervous system due to the 3-hydroxy-5-pregnan-20-one derivative contained therein, and also has excellent stability and can be stored for a long period of time due to the polymorphs of 3-hydroxy-5-pregnan-20-one derivative contained therein. In particular, the pharmaceutical composition is also thermally and mechanically stable, and readily to be prepared into a pharmaceutical preparation.

In a specific embodiment, a disease caused by abnormality of the central nervous system includes, but is not limited to, tremor, epilepsy, depression or an anxiety disorder. In more detail, the disorder of the central nervous system includes, but is not limited to, idiopathic tremor, epilepsy, clinical depression, postnatal or postpartum depression, atypical depression, psychotic major depression, catatonic depression, a seasonal affective disorder, dysthymia, double depression, a depressive personality disorder, recurrent brief depression, a mild depressive disorder, a bipolar disorder or a manic-depressive disorder, a post-traumatic stress disorder, depression due to chronic medical conditions, treatment-resistant depression, refractory depression, suicidal tendency, suicidal ideation or a suicidal behavior.

The pharmaceutical composition of the present invention further comprises optionally a pharmaceutically acceptable carrier. As used herein, the term "composition" is intended to encompass a product comprising a particular amount of a particular ingredient, as well as any product, directly or indirectly, resulting from a combination of a particular amount of a particular ingredient; while a pharmaceutically acceptable carrier refers to a carrier, a diluent or an excipient which does not cause significant irritation to an organism and does not interfere with the biological activity and properties of the compound administered; that is, the carrier, diluent or excipient must be compatible with other ingredients of the preparation and not deleterious to the subject thereof.

The pharmaceutical composition of the present invention may be prepared by a method well known to those skilled in the art. For embodiment, the compound of the present invention may be mixed with a pharmaceutically acceptable carrier, a diluent or an excipient to prepare the corresponding pharmaceutical composition. Further, the compound or pharmaceutical composition of the present invention can be formulated into various suitable dosage forms by those skilled in the art, including, but not limited to the form suitable for rectal administration, transdermal administration, intradermal administration, intrathecal administration, subcutaneous administration, intravenous administration, intramuscular administration, articular cavity administration, oral mucosa administration, vaginal administration, and intranasal administration, etc. Depending on the dosage form required, those skilled in the art can also select the corresponding pharmaceutically acceptable carrier, diluent or excipient.

The pharmaceutical composition of the present invention may contain a safe and effective amount of polymorphs of 3-hydroxy-5-pregnan-20-one derivatives. By "a safe and effective amount", it means that the amount of the compound (or a crystalline form) is sufficient to significantly improve the condition without causing serious side effects. Generally, the pharmaceutical composition contains 30-800 mg of the crystalline form of the invention/dose, preferably 50-600 mg of the crystalline form of the invention/dose. Preferably, said "dose" is a capsule or tablet.

"Pharmaceutically acceptable carrier" means: one or more compatible solid or liquid fillers or gel substances which are suitable for being used in a human and must have sufficient purity and sufficiently low toxicity. "Compatibility", as used herein, means that components of the composition to be admixed with the active ingredient of the invention and with each other without appreciably reducing the efficacy of the active ingredient. Examples of a pharmaceutically acceptable carrier are cellulose and derivatives thereof (e.g., sodium carboxymethylcellulose, sodium ethylcellulose, cellulose acetate, etc.), gelatin, talc, solid lubricants (e.g., stearic acid, magnesium stearate), calcium sulphate, vegetable oils (e.g., soya bean oil, sesame oil, peanut oil, olive oil, etc.), polyols (e.g., propylene glycol, glycerol, mannitol, sorbitol, etc.), emulsifying agents (e.g., Tween®), wetting agent (e.g. sodium dodecyl sulphate), colouring agent, flavouring agent, stabilizer, antioxidant, preservative, pyrogen-free water, etc.

The administration of the polymorphs or pharmaceutical composition of the present invention is not particularly limited, and representative manners for administration include (but are not limited to): oral, rectal, parenteral (intravenous, intramuscular, or subcutaneous), and topical administration.

Solid dosage forms for oral administration include capsules, tablets, pills, dispersions and granules. In these solid dosage forms, the active ingredient is mixed with at least one conventional inert excipient (or carrier), e.g., sodium citrate or dicalcium phosphate, or with following components: (a) fillers or bulking agents, e.g., starch, lactose, sucrose, dextrose, mannitol, and silicic acid; (b) binders, e.g., hydroxymethylcellulose, alginate, gelatin, polyvinylpyrrolidone, sucrose, and gum arabic; (c) humectants, e.g., glycerol; (d) disintegrants, e.g., agar, calcium carbonate, potato starch or tapioca starch, alginate, certain complex silicates, and sodium carbonate; (e) retardants, e.g., paraffin; (f) absorption accelerators, e.g., quaternary amine compounds; (g) wetting agents, e.g., cetearyl alcohols and glycerol monostearate; (h) adsorbents, e.g., kaolin; and (i) lubricants, e.g. talc, calcium stearate, magnesium stearate, solid polyethylene glycol, sodium dodecyl sulfate, or mixtures thereof. In capsules, tablets and pills, the dosage form may also comprise a buffering agent.

Solid dosage forms, such as tablets, sugar pills, capsules, pills and granules may be prepared using coatings and shell materials, such as enteric coatings and other materials well known in the art. They may comprise an opacifying agent, and the active ingredient in such compositions may be released in a delayed manner in a portion of the digestive tract. Examples of encapsulated components that may be employed are polymeric substances and wax-like substances. If necessary, the active ingredient may also be formed in the form of a microcapsule with one or more of the excipients mentioned above.

Liquid dosage forms for oral administration include pharmaceutically acceptable emulsions, solutions, suspensions, syrups or tinctures. In addition to the active ingredient, the liquid dosage form may comprise inert diluents routinely used in the art, such as water or other solvents, solubilising agents and emulsifiers, such as ethanol, isopropanol, ethyl carbonate, ethyl acetate, propylene glycol, 1,3-butylene glycol, dimethylformamide, as well as oils, in particular, cottonseed oil, peanut oil, corn embryo oil, olive oil, castor oil, and sesame oil, or mixtures thereof, and the like.

In addition to these inert diluents, the composition may also comprise auxiliaries such as wetting agents, emulsifiers and suspending agents, sweeteners, flavouring agents and fragrances.

In addition to the active ingredient, the suspension may comprise suspending agents such as, ethoxylated isooctadecanol, polyoxyethylene sorbitol and dehydrated sorbitan esters, microcrystalline cellulose, aluminium methanol and agar, or mixtures thereof.

Compositions for parenteral administration may comprise physiologically acceptable sterile aqueous or non-aqueous solutions, dispersions, suspensions or emulsions, and sterile powders for the re-dissolution into sterile injectable solutions or dispersions. Suitable aqueous and non-aqueous carriers, diluents, solvents or excipients include water, ethanol, polyols and suitable mixtures thereof.

Dosage forms of the polymorphs of the invention for topical administration include ointments, dispersions, patches, sprays and inhalants. The active ingredient is mixed under sterile conditions with a physiologically acceptable carrier and any preservatives, buffers, or propellants that may be required if necessary.

Method for Preventing and Treating Disease

As described above, whereas the 3-hydroxyl-5-pregnane-20-one derivative of the present invention can release an active allopregnanolone under suitable conditions after being administered to a subject. It is understood by a skilled person art that the polymorphs of the 3-hydroxyl-5-pregnane-20-one derivative or a pharmaceutical composition of the present invention can be used for preventing or treating a disorder of the central nervous system, including, but not limited to the above-mentioned disorders of the central nervous system.

The method for preventing or treating a disorder of the central nervous system of the present invention comprises administering a therapeutically effective amount of the above-mentioned compound and pharmaceutical composition to a subject in need thereof.

The subject includes, but is not limited to human.

Advantages of the Invention:

1. In the present invention, polymorphs of the compound of formula I is provided for the first time;
2. Crystalline form A of the compound of Formula I, Crystalline form B of the compound of Formula I and crystalline form C of the compound of Formula I exhibit good stability, low hygroscopicity, good water solubility and good druggability.
3. The preparation process of the crystalline form of the present invention is simple, thereby possessing excellent potential for industrialisation and implementation.

The present invention is further described below in conjunction with specific embodiments. It is to be understood that these embodiments serve only to illustrate the present invention and are not limiting the scope of the present invention. In the following embodiments, experimental methods without specifying specific conditions are generally performed under conventional conditions or following the manufacturer's recommended conditions. Percentages and parts are by weight unless otherwise specified.

Detection Methods:

XRPD (X-ray Powder Diffraction) Method 1: about 10 mg of a sample is uniformly laid on a single crystal silicon sample disc, and XRPD detection is performed using following parameters. Instrument model: X'Pert$^3$ X-ray diffractometer; target: Cu-Kα (40 mA, 45 kV); scanning range from 3° to 40° in the 2θ interval.

XRPD (X-ray Powder Diffraction) Method 2: about 10 mg of sample is uniformly laid on a single crystal silicon sample disc, and XRPD detection is performed using following parameters. Instrument model: BRUKER D8 X-ray diffractometer; target: Cu-Kα (40 kV, 40 mA). The scanning range is from 3° to 40° in the 2θ interval and the scanning speed is 8°/min.

Measurement variations associated with the results of such X-ray powder diffraction analyses arise from a variety of factors, including (a) errors in the sample preparation (e.g., sample height), (b) instrumentation errors, (c) calibration variations, (d) operator's errors (including those that occur when determining peak positions), and (e) the nature of a substance (e.g., a preferred orientation error). Calibration errors and errors in sample height often result in displacement of all peaks in the same direction. When a flat holder is used, small differences in sample height will result in large displacements in XRPD peak positions. Systematic studies have shown that a 1 mm difference in sample height can result in peak displacements as high as 1° at 2θ. These displacements can be identified from the X-ray diffractograms and can be eliminated by either compensating for said displacements (applying the system calibration factor to all peak position values) or by recalibrating the instrument. Measurement errors from different instruments can be corrected by applying a system calibration factor to force the peak positions consistent, as described above.

TGA (Thermogravimetric Analysis) method: Instrument model: TA Q500 Thermogravimetric Analyser with $N_2$ atmosphere and a heating rate of 10° C./min.

DSC (Differential Scanning Calorimetry) method: Instrument model: METTLER TOLEDO DSC3+ with $N_2$ atmosphere and a heating rate of 10° C./min.

Example 1. Synthesis of the Compound of Formula I

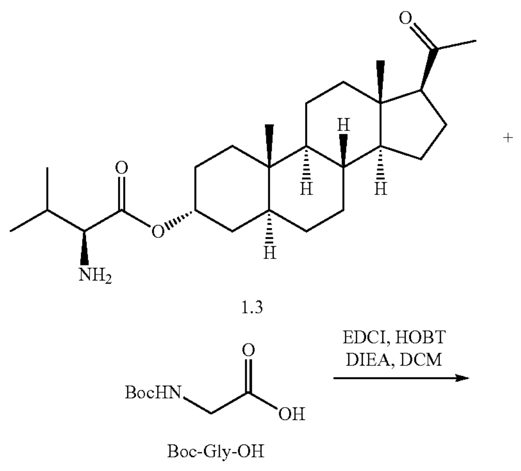

1.3

Boc-Gly-OH

-continued

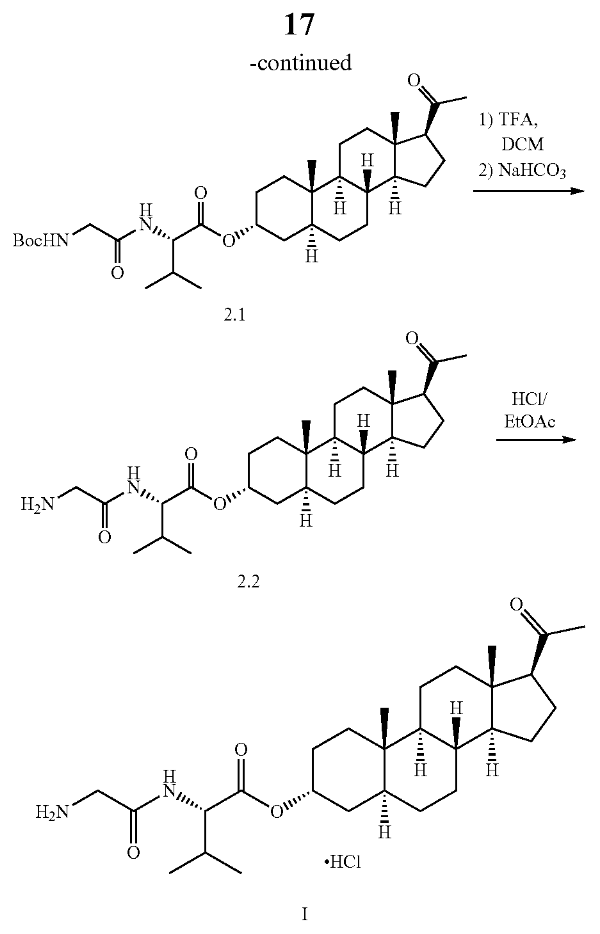

2.1

2.2

I

Preparation of Intermediate 2.1:

Compound 1.3 (5.0 g, 12.0 mmol), Boc-Gly-OH (2.5 g, 14.3 mmol), and dichloromethane (50 mL) were added into a 250 mL single-neck reaction flask, and magnetically stirred. Then, N,N-diisopropylethylamine (3.1 g, 24.0 mmol), HOBT (342 mg, 2.4 mmol), and EDCI (2.8 g, 14.6 mmol) were added. The mixture was reacted at room temperature for 4 hours, and the reaction solution was washed with $H_2O$ (50 mL), 1N HCl (50 mL), a saturated aqueous solution of $NaHCO_3$, and pure water. The reaction solution was concentrated under a reduced pressure, and the crude product was subjected to column chromatography (petroleum ether (60-90)/ethyl acetate 10:1-3:1) to obtain an off-white solid (5.7 g, yield 82.8%).

Preparation of Intermediate 2.2:

Compound 2.1 (5.5 g, 9.63 mmol, 1.0 eq), and dichloromethane (22 mL) were added into a 250 mL three-neck reaction flask. Under nitrogen protection and magnetic stirring, trifluoroacetic acid (10.9 g, 95.7 mmol) was added at 0° C., then reacted at room temperature for 3 hours. The mixture was concentrated under a reduced pressure, and evaporated to remove the solvent. Dichloromethane (50 mL) was added, a saturated aqueous solution of sodium bicarbonate was used for washing, and an aqueous phase was extracted with dichloromethane (30 mL). The organic phase was combined, then washed with 50 mL of pure water and dried over anhydrous sodium sulfate. It was filtered and concentrated under a reduced pressure, and vacuum-dried using an oil pump to obtain an off-white solid (4.5 g, yield 99.0%).

Preparation of the Compound of Formula I:

Compound 2.2 (4.5 g, 9.5 mmol, 1.0 eq), and ethyl acetate (27 mL) were added into a 250 mL single-neck reaction flask. Under nitrogen protection and magnetic stirring, a solution of hydrogen chloride in ethyl acetate (3 M, 3.8 mL, 11.4 mmol) was added at room temperature, and stirred for another 1 hour. The mixture was concentrated under a reduced pressure, and evaporated to remove the solvent. Acetonitrile (70 mL) was added and stirred at room temperature for 2 hours. After filtration, the solid was washed with acetonitrile (15 mL). An oil pump was used for vacuum drying at 40° C. for 2 hours to obtain a white solid (3.5 g, yield 72.2%).

$^1H$ NMR (400 MHz, $CDCl_3$) δ 8.28 (d, J=8.5 Hz, 1H), 8.16 (bs, 3H), 5.14-5.03 (m, 1H), 4.55 (d, J=4.1 Hz, 1H), 4.27 (d, J=16.1 Hz, 1H), 4.09 (d, J=16.0 Hz, 1H), 2.52 (t, J=8.7 Hz, 1H), 2.40-2.07 (m, 2H), 2.11 (s, 3H), 2.05-1.96 (m, 1H), 1.82-1.08 (m, 18H), 1.08-0.89 (m, 7H), 0.85-0.71 (m, 1H), 0.79 (s, 3H), 0.61 (s, 3H).

MS: m/z [M+H]+ 475.3.

Example 2. Preparation of Crystalline Form A of the Compound of Formula I

To a 100 ml flask was added 60 ml of ethyl acetate, 10.0 g of the compound of formula I. The obtained mixture was heated to 60-65° C., suspended and stirred for 6 h-24 h, then cooled to 20-30° C., filtered and dried to give white solids.

Figure 2:
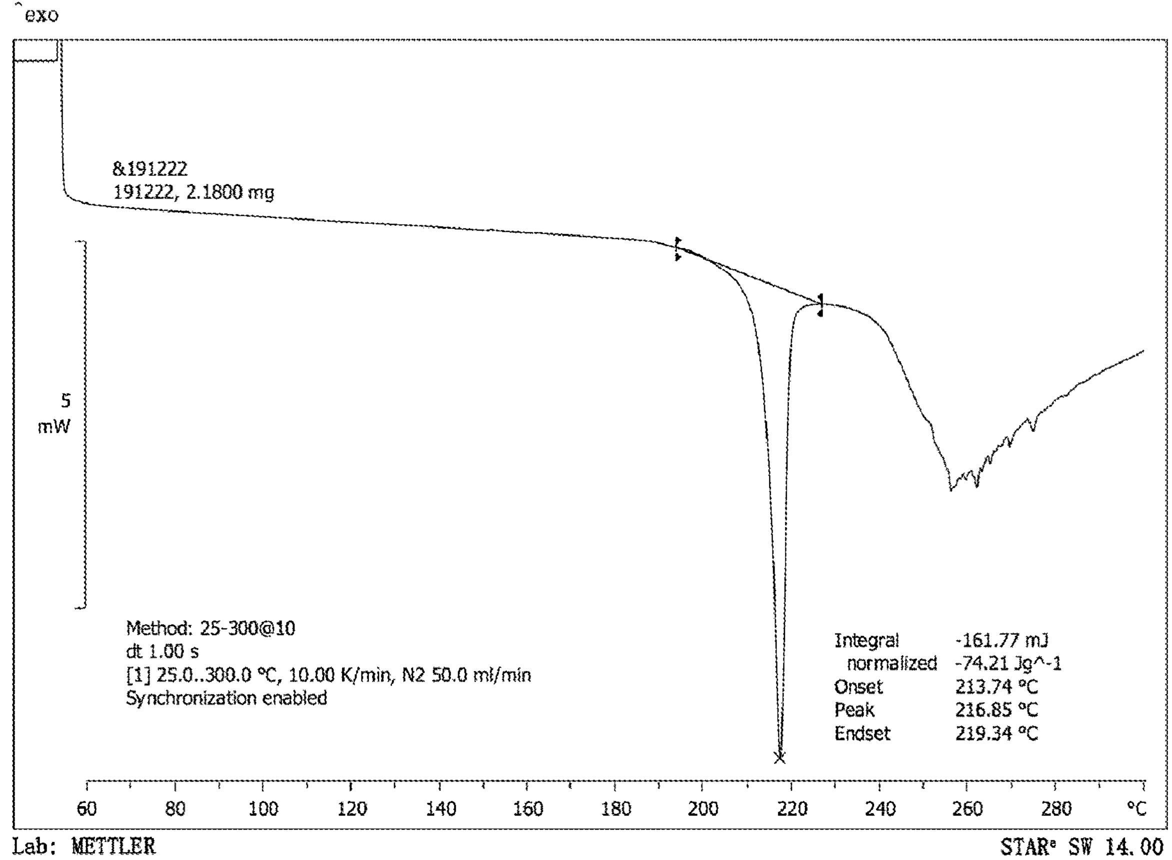
FIG. 2 shows DSC pattern of crystalline form A of the 3-hydroxy-5-pregnan-20-one derivative of the present invention.

The XRPD pattern (measured using XRPD method 1) and DSC pattern of the resulting crystalline form were tested as being essentially shown in FIGS. 1 and 2, respectively. The diffraction angle data of the XRPD pattern of the resulting crystalline form are essentially shown in Table 7, wherein the error range of 2θ values is ±0.2°.

TABLE 7

XRPD resolution data for crystalline form A

| number | 2θ angle (°) | interplanar spacing (Å) | relative intensity (%) |
|---|---|---|---|
| 1 | 11.96 | 7.40 | 21.12 |
| 2 | 12.66 | 7.00 | 23.74 |
| 3 | 13.53 | 6.54 | 49.52 |
| 4 | 13.88 | 13.88 | 8.31 |
| 5 | 14.51 | 6.11 | 19.45 |
| 6 | 15.81 | 5.60 | 11.30 |
| 7 | 16.75 | 5.29 | 53.89 |
| 8 | 17.99 | 4.93 | 13.11 |
| 9 | 18.99 | 4.67 | 13.44 |
| 10 | 19.27 | 4.61 | 16.18 |
| 11 | 21.95 | 4.05 | 12.16 |
| 12 | 22.19 | 4.01 | 58.99 |
| 13 | 25.39 | 3.51 | 100.00 |
| 14 | 26.23 | 3.40 | 18.60 |
| 15 | 31.87 | 2.81 | 58.49 |
| 16 | 35.34 | 2.54 | 20.81 |

Example 3. Preparation of Crystalline Form B of the Compound of Formula I

To a 100 ml flask was added 60 ml of purified water, 10.0 g of compound of formula I. The obtained mixture was heated to 65-75° C., stirred until the solid was dissolved, and then cooled to 2-8° C. until the precipitation of crystals was complete, filtered, and dried to give white solids.

Figure 3:
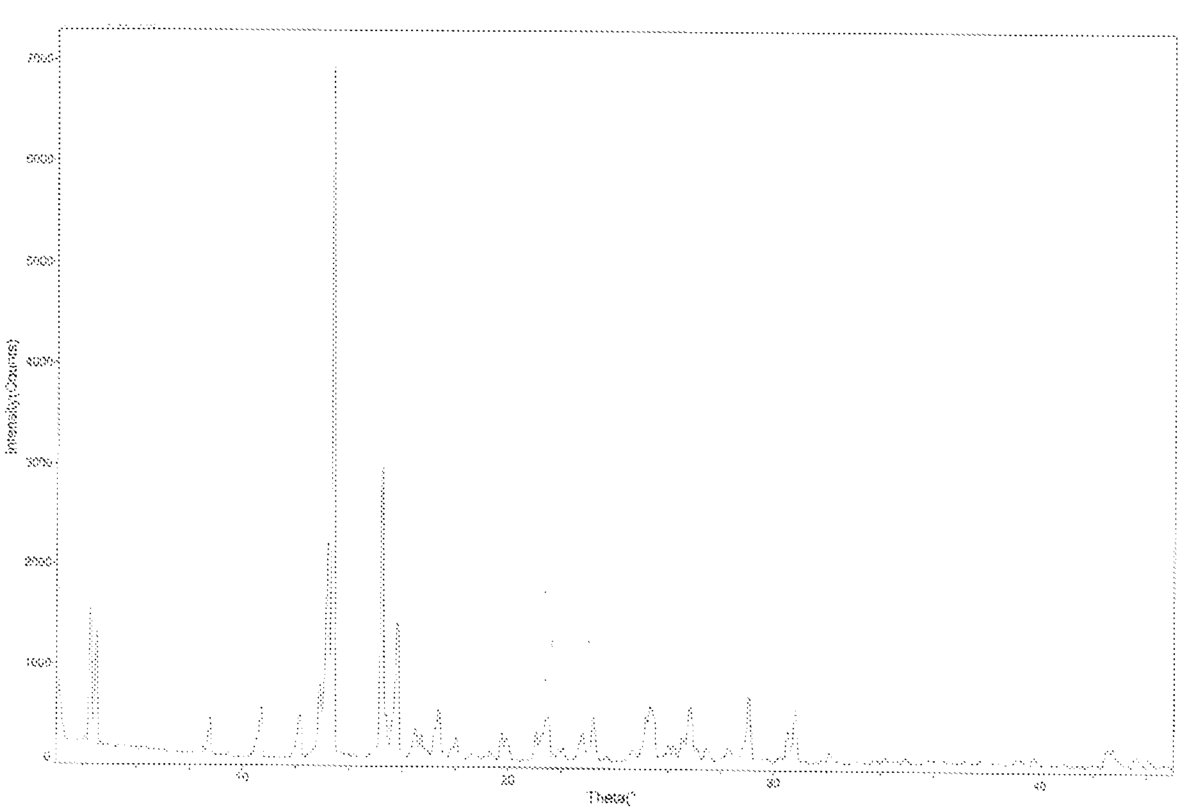
FIG. 3 shows XRPD pattern of crystalline form B of the 3-hydroxy-5-pregnan-20-one derivative of the present invention.

The XRPD pattern (measured using XRPD method 2) of the resulting crystalline form B were tested as being essentially shown in FIG. 3. The diffraction angle data of the XRPD pattern of the resulting crystalline form are basically shown in Table 8, wherein the error range of 2θ values is ±0.2°.

TABLE 8

XRPD resolution data for crystalline form B

| number | 2θ angle (°) | interplanar spacing (Å) | relative intensity (%) |
|---|---|---|---|
| 1 | 4.260 | 20.7270 | 17.6 |
| 2 | 4.497 | 19.6332 | 14.7 |
| 3 | 8.773 | 10.0716 | 7.6 |
| 4 | 10.686 | 8.2718 | 11.5 |
| 5 | 12.143 | 7.2823 | 6.7 |
| 6 | 12.876 | 6.8696 | 27.9 |
| 7 | 13.171 | 6.7162 | 62.5 |
| 8 | 13.366 | 6.6186 | 100 |
| 9 | 15.223 | 5.8154 | 47.6 |
| 10 | 15.813 | 5.5998 | 27.2 |
| 11 | 17.371 | 5.1008 | 10.1 |
| 12 | 21.469 | 4.1355 | 20.5 |
| 13 | 23.186 | 3.8330 | 12.1 |
| 14 | 25.351 | 3.5103 | 21.4 |
| 15 | 26.831 | 3.3200 | 15.4 |
| 16 | 29.038 | 3.0725 | 15.0 |
| 17 | 30.518 | 2.9268 | 11.2 |
| 18 | 30.792 | 2.9014 | 13.1 |

Figure 4:
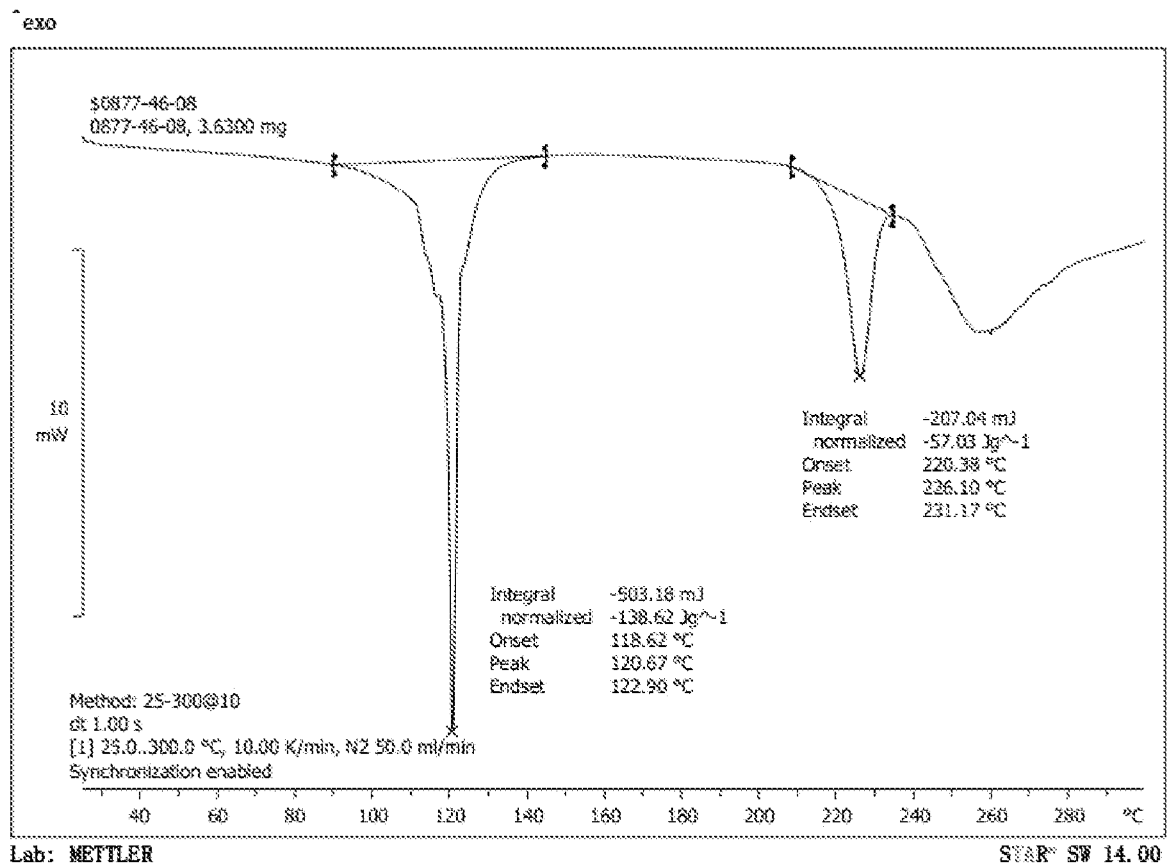
FIG. 4 shows DSC pattern of crystalline form B of the 3-hydroxy-5-pregnan-20-one derivative of the present invention.

The DSC pattern of the obtained crystalline form B was tested as being essentially shown in FIG. 4, and the differential scanning calorimetry curve of crystalline form B has endothermic peaks near 120.67° C. and 226.10° C., indicating that crystalline form B might be a hydrate.

Figure 5:
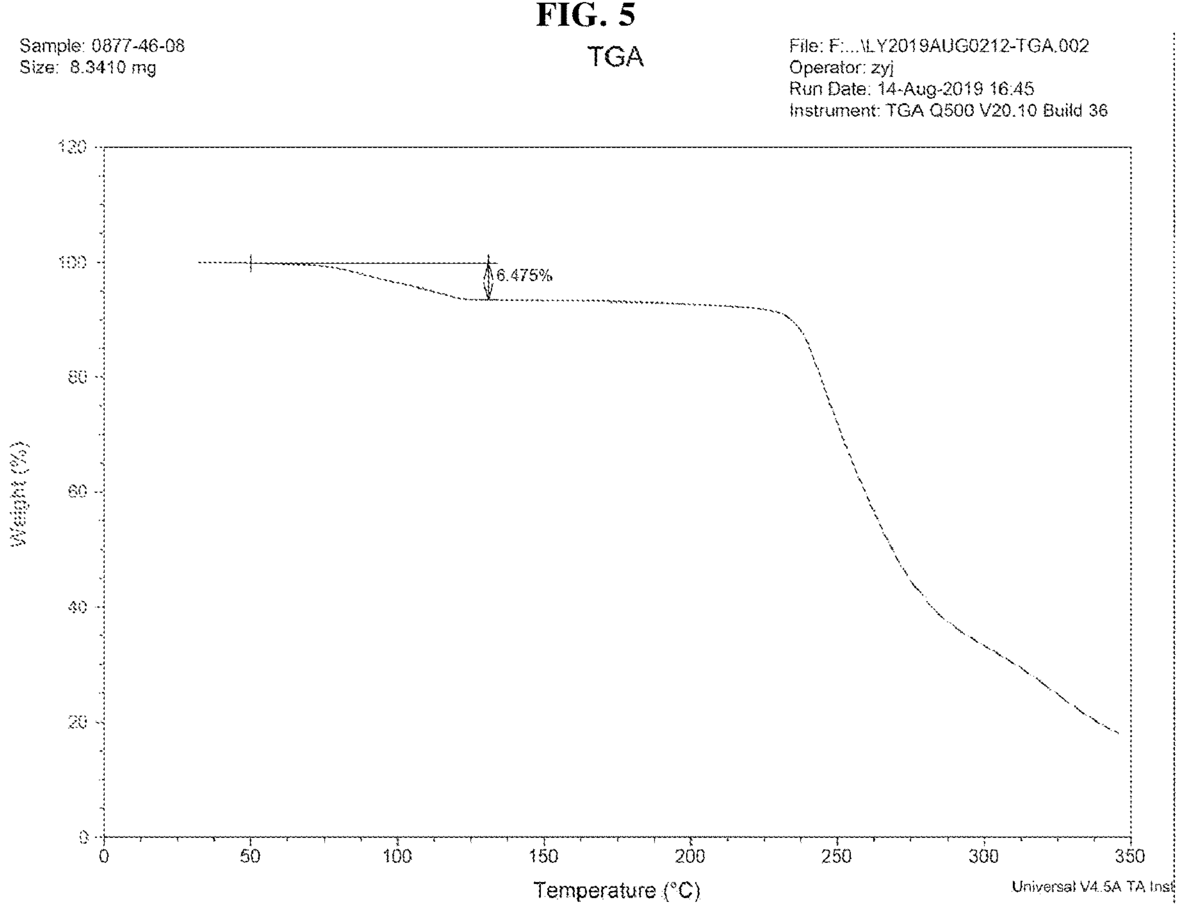
FIG. 5 shows TGA pattern of crystalline form B of the 3-hydroxy-5-pregnan-20-one derivative of the present invention.

The TGA pattern of the resulting crystalline form B was further tested as being essentially shown in FIG. 5. From this pattern, it can be seen that there is a weight loss of 6.475±0.5%. Therefore, crystalline form B should be a dihydrate.

Example 4. Preparation of Crystalline Form C of the Compound of Formula I

To a 250 ml flask was added 40 ml of ethanol and 10.0 g of the compound of formula I. The obtained mixture was heated to 65-75° C., stirred until the solid was dissolved, and then 80 ml of methyl tert-butyl ether was added, cooled to 2-8° C. until the precipitation of crystals was complete, filtered, and dried to give white solids.

Figure 6:
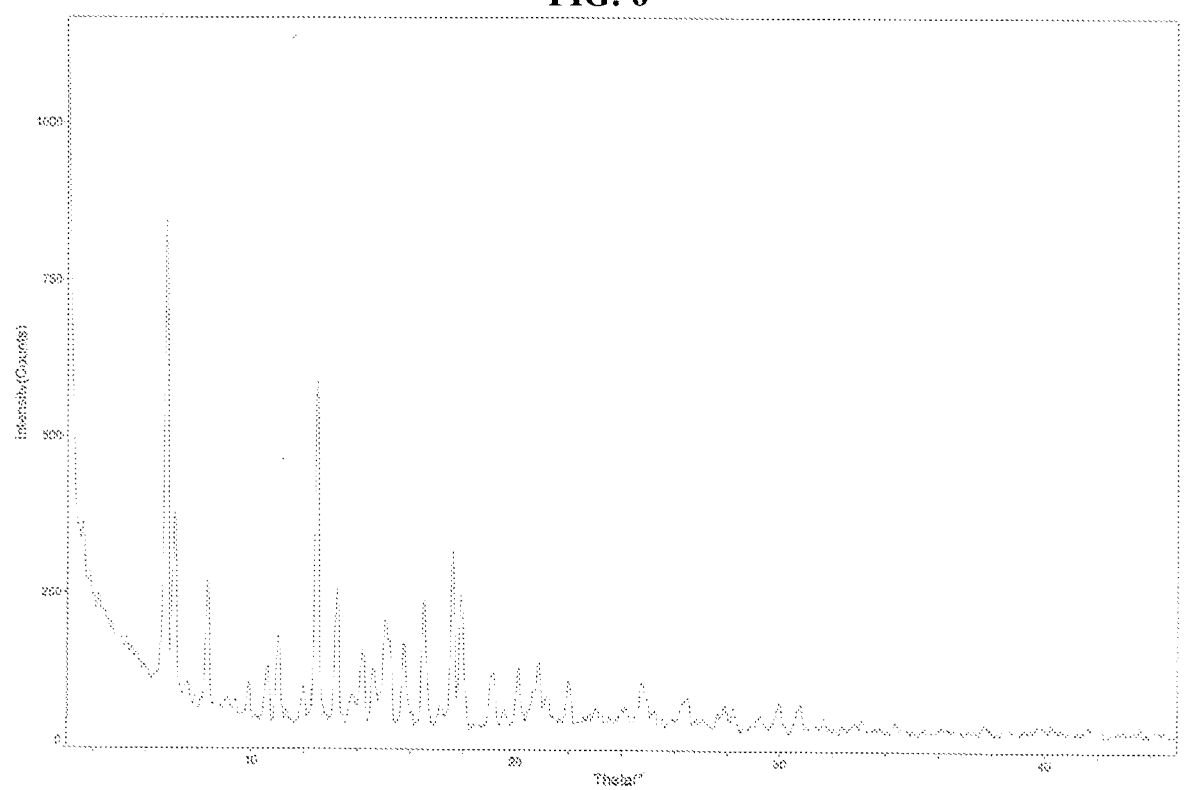
FIG. 6 shows XRPD pattern of crystalline form C of the 3-hydroxy-5-pregnan-20-one derivative of the present invention.
Figure 7:
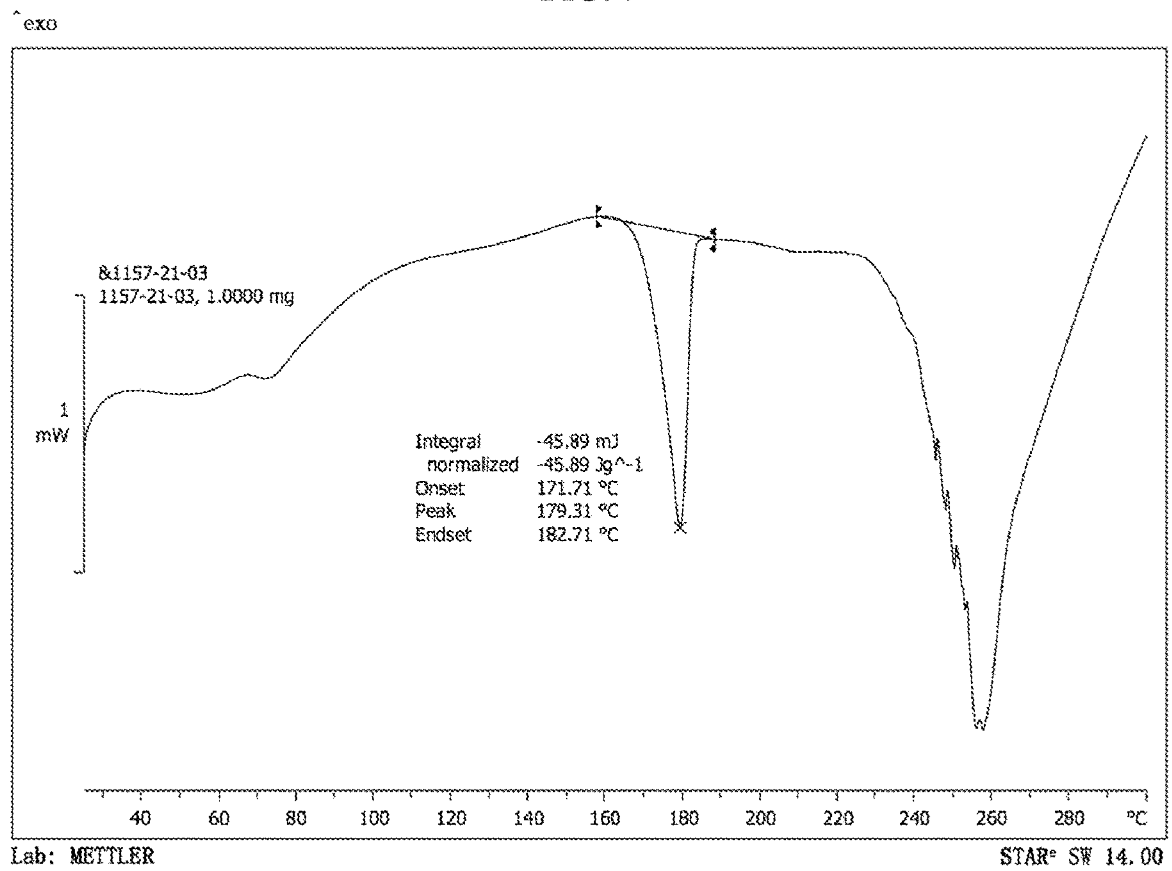
FIG. 7 shows DSC pattern of crystalline form C of the 3-hydroxy-5-pregnan-20-one derivative of the present invention.

The XRPD pattern (measured using XRPD method 2) and DSC pattern of the resulting crystalline form were tested as being essentially shown in FIGS. 6 and 7, respectively. The diffraction angle data of the XRPD pattern of the resulting crystalline form are essentially shown in Table 9, wherein the error range of 2θ values is ±0.2°.

TABLE 9

XRPD resolution data for crystalline form C

| number | 2θ angle (°) | interplanar spacing (Å) | relative intensity (%) |
|---|---|---|---|
| 1 | 6.766 | 13.0535 | 100.00 |
| 2 | 7.079 | 12.4772 | 43.9 |
| 3 | 8.342 | 10.5905 | 25.0 |
| 4 | 10.608 | 8.3326 | 10.7 |
| 5 | 11.024 | 8.0195 | 19.5 |
| 6 | 12.462 | 7.0970 | 71.8 |
| 7 | 13.212 | 6.6958 | 23.2 |
| 8 | 13.764 | 6.4284 | 11.4 |
| 9 | 14.197 | 6.2333 | 19.8 |
| 10 | 14.629 | 6.0503 | 15.9 |
| 11 | 15.063 | 5.8767 | 38.8 |
| 12 | 15.753 | 5.6210 | 16.4 |
| 13 | 16.521 | 5.3613 | 27.3 |
| 14 | 17.605 | 5.0336 | 47.5 |
| 15 | 17.921 | 4.9455 | 34.1 |
| 16 | 19.143 | 4.6324 | 17.0 |
| 17 | 20.858 | 4.2552 | 27.5 |
| 18 | 24.762 | 3.5925 | 20.7 |
| 19 | 26.457 | 3.3661 | 13.6 |

Example 5 Study on Polymorphs of the Compound of Formula I

Crystalline form A of the compound of formula I was heated, suspended and pulped in corresponding solvents and stirred for 2 days at 40° C. in darkness. The solution was centrifuged to remove the precipitates, which were dried and assayed by XPRD as follows:

| Number | Solvent | Crystalline form |
|---|---|---|
| 1 | Ethyl acetate | Crystalline form A |
| 2 | Ethanol | Crystalline form A |
| 3 | Acetone | Crystalline form A |
| 4 | Methyl tert-butyl ether | Crystalline form A |
| 5 | n-Heptane | Crystalline form A |
| 6 | Toluene | Crystalline form A |
| 7 | Methanol | Crystalline form A |

After analysing the results in the above table, it is concluded that crystalline form A exhibits good stability and remains stable in different solvent systems.

Example 6. Study on Mechanical Stability of Crystalline Form A

Crystalline form A of the compound of formula I was treated under corresponding mechanical conditions and certain samples were taken and tested by XRPD with the following results:

| number | mechanical condition | Crystalline form |
|---|---|---|
| 1 | Ground in an agate mortar for a few minutes | Crystalline form A |
| 2 | pulverised in a mechanical shredder for a few minutes | Crystalline form A |
| 3 | pressed in a tablet press | Crystalline form A |

After analysing the results in the above table, it is concluded that grinding, mechanical pulverising and pressure did not result in the transcrystallisation of crystalline forme A, that is, grinding, mechanical pulverising and pressure have no effects on the stability of crystalline form A.

Example 7. Study on Accelerated Stability Test of Crystalline Form A

Crystalline form A obtained in Example 1 was placed in an open and flat position and left at high temperature and high humidity (40° C., RH75%) for 3 months, and certain samples were taken at 1 month, 2 months, and 3 months, respectively, to test the XRPD pattern for evaluating the stability of crystalline form A.

Figure 8:
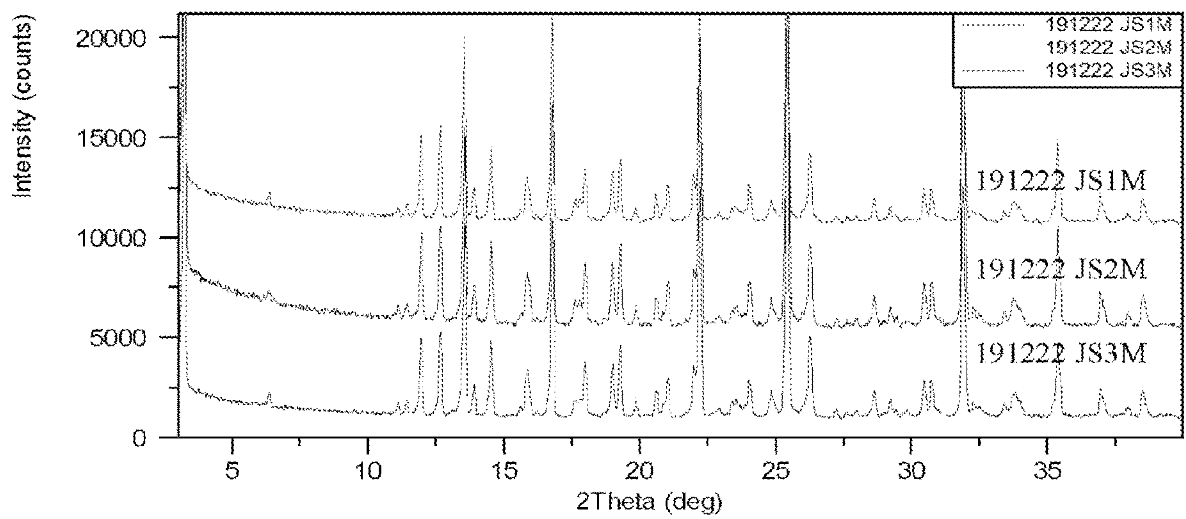
FIG. 8 shows the XRPD superposition pattern of crystalline form A of the 3-hydroxy-5-pregnan-20-one derivative of the present invention after placed at room temperature for 1 month (191222 JS1M), 2 months (191222 JS2M), and 3 months (191222 JS3M).

From the experiment and XRPD pattern (measured by XRPD method 1), it can be seen that the XRPD pattern of crystalline form A at month 1 (191222 JS1M), month 2 (191222 JS2M), and month 3 (191222 JS3M) are substantially the same as that of crystalline form A shown in FIG. 1, and crystalline form A exhibits good stability, and there is no change of crystalline type A after the accelerated stability test for 3 months, which is shown in FIG. 8.

Example 8. Study on Physical Stability of Crystalline Form

Crystalline form A, crystalline form B and crystalline form C obtained in Example 1 were placed in an open and flat position to examine the stability of the samples under high temperature (60° C.), high humidity (RH92.5%), and light (4500±500 Lux) conditions. The samples were examined for 5, 10 and 30 days and the purities tested by HPLC assay are shown in Table 10.

TABLE 10

Experiment on stability of crystalline forms

| sample | time (day) | high temperature (60° C.) | high humidity (RH92.5%) | light (4500 ± 500 Lux) |
|---|---|---|---|---|
| crystalline | 0 | 99.69% | 99.69% | 99.69% |
| form A | 5 | 99.62% | 99.69% | 99.66% |
| | 10 | 99.68% | 99.69% | 99.70% |
| | 30 | 99.69% | 99.69% | 99.67% |
| crystalline | 0 | 99.59% | 99.59% | 99.59% |
| form B | 5 | 99.57% | 99.58% | 99.55% |
| | 10 | 99.54% | 99.55% | 99.53% |
| | 30 | 99.52% | 99.56% | 99.52% |
| crystalline | 0 | 99.62% | 99.62% | 99.62% |
| form C | 5 | 99.61% | 99.58% | 99.60% |
| | 10 | 99.59% | 99.56% | 99.59% |
| | 30 | 99.60% | 99.53% | 99.57% |

After analysing the results in the above table, it is concluded that crystalline form A, crystalline form B and crystalline form C are stable under high temperature, high humidity and light conditions, and exhibit good druggability.

All documents mentioned in this application are hereby incorporated by reference as if each document were individually incorporated by reference. In addition, it should be understood that after reading the above teachings of the invention, those skilled in the art can make various changes or modifications to the invention, and these equivalent forms also fall within the scope defined by the appended claims of this application.

The invention claimed is:

1. A crystalline form A of a compound of formula I and the X-ray powder diffraction pattern thereof shows characteristic peaks at following 2θ angles: 12.66±0.2°, 13.53±0.2°, 16.75±0.2° and 25.39±0.2°;

I

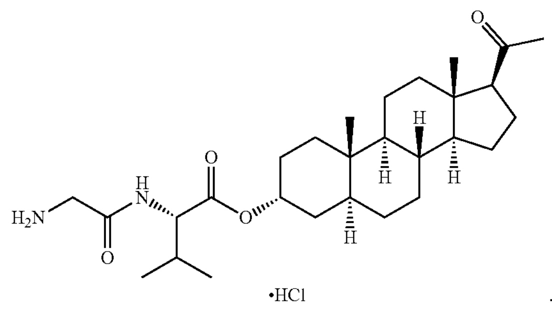

•HCl

.

2. The crystalline form A of a compound of formula I according to claim 1, wherein the X-ray powder diffraction pattern of the crystalline form A shows characteristic peaks at following 2θ angles: 11.96±0.2°, 12.66±0.2°, 13.53±0.2°, 14.51±0.2°, 16.75±0.2° and 25.39±0.2°.

3. A crystalline form B of a compound of formula I and the X-ray powder diffraction pattern thereof shows characteristic peaks at following 2θ angles: 10.69±0.2°, 13.17±0.2°, 13.37±0.2° and 15.22±0.2°

I

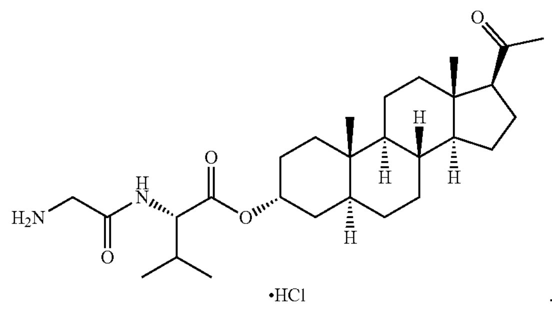

•HCl

.

4. The crystalline form B of a compound of formula I according to claim 3, wherein the X-ray powder diffraction pattern of the crystalline form B shows characteristic peaks at following 2θ angles: 4.26±0.2°, 4.50±0.2°, 10.69±0.2°, 13.17±0.2°, 13.37±0.2°, and 15.22±0.2°.

5. A crystalline form C of a compound of formula I and the X-ray powder diffraction pattern thereof shows characteristic peaks at following 2θ angles: 6.77±0.2°, 7.08±0.2°, 8.34±0.2° and 12.46±0.2°;

I

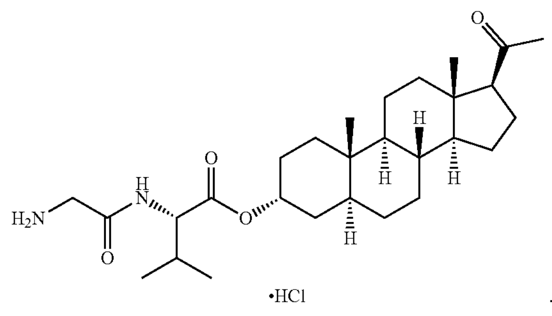

•HCl

.

6. The crystalline form C of a compound of formula I according to claim 5, wherein the X-ray powder diffraction pattern of the crystalline form C shows characteristic peaks at following 2θ angles: 6.77±0.2°, 7.08±0.2°, 8.34±0.2°, 12.46±0.2°, 17.60±0.2° and 17.92±0.2°.

7. A pharmaceutical composition, and said pharmaceutical composition comprises a crystalline form A, crystalline form B or crystalline form C of a compound of formula and optionally a pharmaceutically acceptable excipient;

I

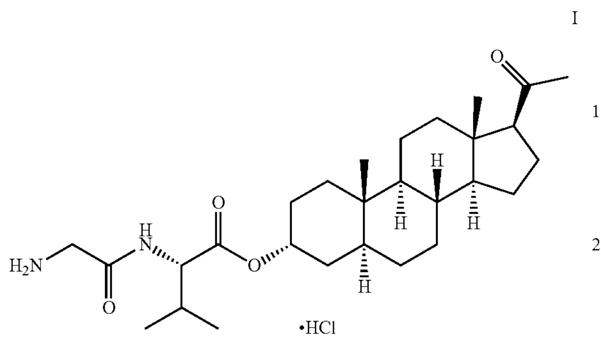

wherein the X-ray powder diffraction pattern of the crystalline form A shows characteristic peaks at following 2θ angles: 12.66±0.2°, 13.53±0.2°, 16.75±0.2° and 25.39±0.2°; or, the X-ray powder diffraction pattern of the crystalline form A further shows characteristic peaks at following 2θ angles: 11.96±0.2°, 12.66±0.2°, 13.53±0.2°, 14.51±0.2°, 16.75±0.2° and 25.39±0.2°;

the X-ray powder diffraction pattern of the crystalline form B shows characteristic peaks at following 2θ angles: 10.69±0.2°, 13.17±0.2°, 13.37±0.2° and 15.22±0.2°; or, the X-ray powder diffraction pattern of the crystalline form B further shows characteristic peaks at following 2θ angles: 4.26±0.2°, 4.50±0.2°, 10.69±0.2°, 13.17±0.2°, 13.37±0.2°, and 15.22±0.2°; and the X-ray powder diffraction pattern of the crystalline form C shows characteristic peaks at following 2θ angles: 6.77±0.2°, 7.08±0.2°, 8.34±0.2° and 12.46±0.2°; or the X-ray powder diffraction pattern of the crystalline form C further shows characteristic peaks at following 2θ angles: 6.77±0.2°, 7.08±0.2°, 8.34±0.2°, 12.46±0.2°, 17.60±0.2° and 17.92±0.2°.

8. The pharmaceutical composition according to claim 7, where in said pharmaceutical composition comprises the crystalline form A and optionally a pharmaceutically acceptable excipient.

9. A method for treating or preventing a disorder of the central nervous system in a mammal, wherein said method comprises administering to the mammal a therapeutically effective amount of a compound of formula (I), crystalline form A, a pharmaceutical composition comprising the crystalline form A, crystalline form B, a pharmaceutical composition comprising the crystalline form B, crystalline form C, and a pharmaceutical composition comprising the crystalline form C;

I

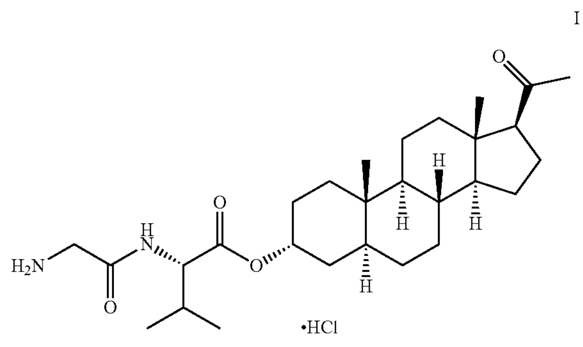

wherein the X-ray powder diffraction pattern of the crystalline form A shows characteristic peaks at following 2θ angles: 12.66±0.2°, 13.53±0.2°, 16.75±0.2° and 25.39±0.2°; or, the X-ray powder diffraction pattern of the crystalline form A further shows characteristic peaks at following 2θ angles: 11.96±0.2°, 12.66±0.2°, 13.53±0.2°, 14.51±0.2°, 16.75±0.2° and 25.39±0.2°;

the X-ray powder diffraction pattern of the crystalline form B shows characteristic peaks at following 2θ angles: 10.69±0.2°, 13.17±0.2°, 13.37±0.2° and 15.22±0.2°; or, the X-ray powder diffraction pattern of the crystalline form B further shows characteristic peaks at following 2θ angles: 4.26±0.2°, 4.50±0.2°, 10.69±0.2°, 13.17±0.2°, 13.37±0.2°, and 15.22±0.2°; and the X-ray powder diffraction pattern of the crystalline form C shows characteristic peaks at following 2θ angles: 6.77±0.2°, 7.08±0.2°, 8.34±0.2° and 12.46±0.2°; or the X-ray powder diffraction pattern of the crystalline form C further shows characteristic peaks at following 20 angles: 6.77±0.2°, 7.08±0.2°, 8.34±0.2°, 12.46±0.2°, 17.60±0.2° and 17.92±0.2°.

* * * * *